United States Patent
Teoh

(10) Patent No.: US 10,682,495 B2
(45) Date of Patent: Jun. 16, 2020

(54) NEEDLE DEVICES WITH ADJUSTABLE GRIPS AND RELATED METHODS

(71) Applicant: B. Braun Melsungen AG, Melsungen (DE)

(72) Inventor: Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 743 days.

(21) Appl. No.: 14/974,487

(22) Filed: Dec. 18, 2015

(65) Prior Publication Data

US 2017/0173304 A1 Jun. 22, 2017

(51) Int. Cl.
*A61M 25/00* (2006.01)
*A61M 25/06* (2006.01)
*A61M 5/162* (2006.01)

(52) U.S. Cl.
CPC .... *A61M 25/0097* (2013.01); *A61M 25/0606* (2013.01); *A61M 5/1626* (2013.01); *A61M 2205/586* (2013.01); *A61M 2207/00* (2013.01)

(58) Field of Classification Search
CPC .......... A61M 25/0693; A61M 25/0637; A61M 25/0097
See application file for complete search history.

(56) References Cited

U.S. PATENT DOCUMENTS

| | | | | |
|---|---|---|---|---|
| 4,013,080 A | * | 3/1977 | Froning | A61B 17/3401 604/165.01 |
| 4,209,015 A | * | 6/1980 | Wicks | A61M 25/02 604/165.03 |
| 4,973,313 A | * | 11/1990 | Katsaros | A61M 25/0097 604/165.02 |
| 8,337,461 B2 | * | 12/2012 | Burkholz | A61M 25/0637 604/164.01 |
| 8,357,121 B2 | * | 1/2013 | Burkholz | A61M 25/0612 604/164.01 |
| 2007/0270758 A1 | * | 11/2007 | Hanner | A61M 25/0606 604/177 |

(Continued)

FOREIGN PATENT DOCUMENTS

| | | | |
|---|---|---|---|
| EP | 1293228 A2 * | 3/2003 | ........ A61M 39/0613 |
| EP | 1293228 A2 | 3/2003 | |

(Continued)

OTHER PUBLICATIONS

International Preliminary Report on Patentability (Chapter I) on corresponding PCT application (PCT/EP2016/081422) from International Searching Authority (EPO) dated Jun. 28, 2018.

(Continued)

*Primary Examiner* — Nathan R Price
*Assistant Examiner* — Mark A Igel
(74) *Attorney, Agent, or Firm* — Klein, O'Neill & Singh, LLP

(57) ABSTRACT

A needle device, such as a catheter assembly, includes a catheter tube attached to a catheter hub, a needle attached to a needle hub, and an optional needle guard for covering the needle tip in a protective position. Different markets can utilize the same needle device by separately forming an extension clip having a gripping member or gripping pad for attaching to the needle device for those markets that require the gripping member or pad.

64 Claims, 9 Drawing Sheets

(56) References Cited

U.S. PATENT DOCUMENTS

| | | | | |
|---|---|---|---|---|
| 2009/0163871 A1* | 6/2009 | Burkholz | A61M 25/0606 604/164.08 |
| 2010/0249713 A1* | 9/2010 | Burkholz | A61M 25/0612 604/177 |
| 2010/0249714 A1* | 9/2010 | Burkholz | A61M 25/0637 604/177 |
| 2011/0009717 A1* | 1/2011 | Davis | A61B 5/1405 600/309 |
| 2012/0016302 A1* | 1/2012 | Stout | A61M 25/0693 604/122 |
| 2012/0016307 A1* | 1/2012 | Burkholz | A61B 5/1422 604/168.01 |
| 2013/0090608 A1* | 4/2013 | Stout | A61M 25/0097 604/256 |
| 2016/0008582 A1* | 1/2016 | Burkholz | A61M 25/0625 604/164.08 |
| 2016/0331936 A1* | 11/2016 | Lim | A61M 5/158 |
| 2016/0354580 A1* | 12/2016 | Teoh | A61M 25/0097 |
| 2016/0361519 A1* | 12/2016 | Teoh | A61M 25/0097 |
| 2017/0120011 A1* | 5/2017 | Burkholz | A61M 25/0097 |
| 2017/0120015 A1* | 5/2017 | Burkholz | A61M 25/0606 |
| 2017/0120016 A1* | 5/2017 | Burkholz | A61M 25/0606 |
| 2017/0120017 A1* | 5/2017 | Burkholz | A61M 25/0606 |

FOREIGN PATENT DOCUMENTS

| | | | |
|---|---|---|---|
| WO | WO 2010/111283 A1 | 9/2010 | |
| WO | WO-2010111283 A1 * | 9/2010 | ........ A61M 25/0612 |

OTHER PUBLICATIONS

International Search Report and Written Opinion on corresponding PCT application (PCT/EP2016/081422) from International Searching Authority (EPO) dated Mar. 10, 2017.

* cited by examiner

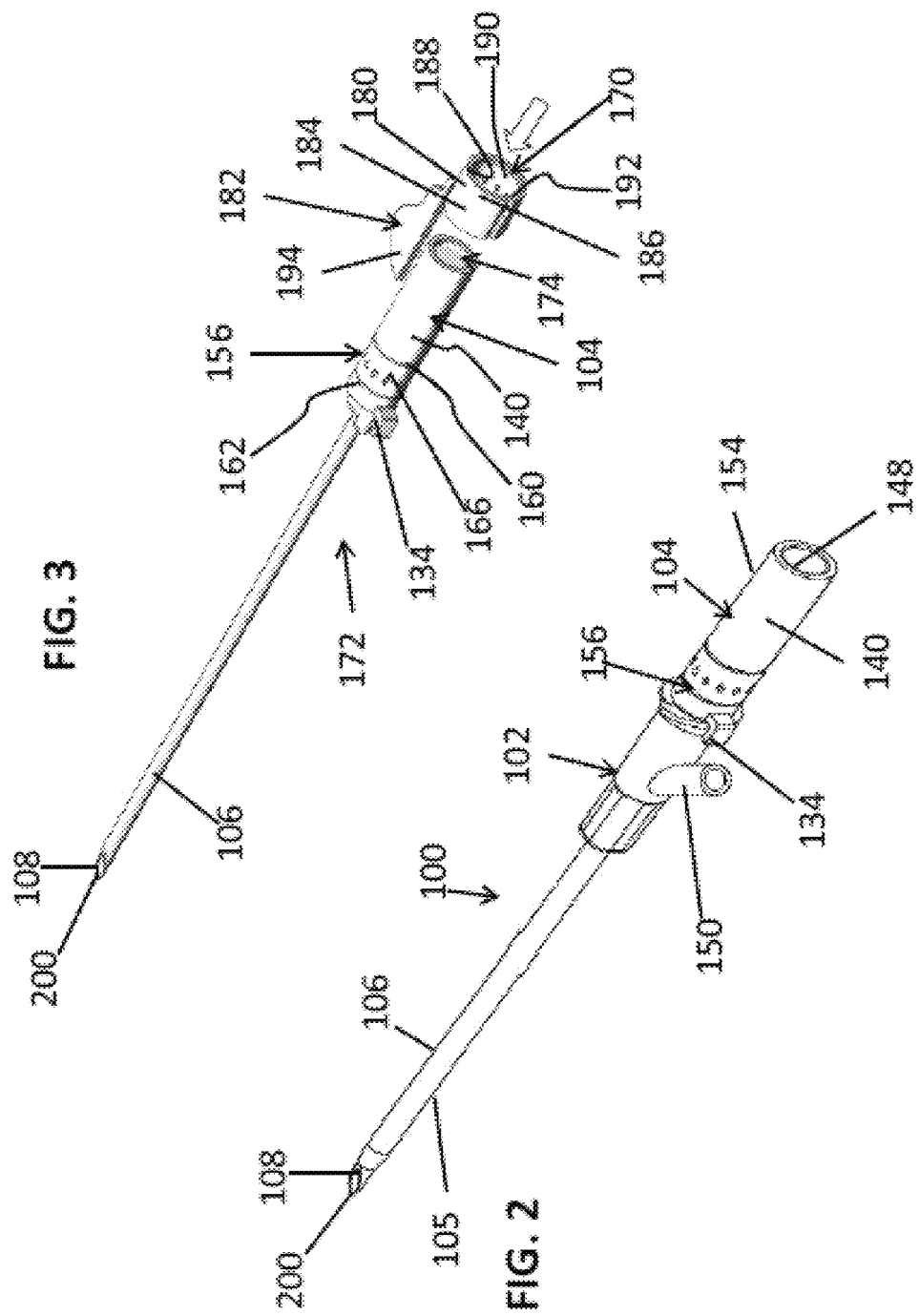

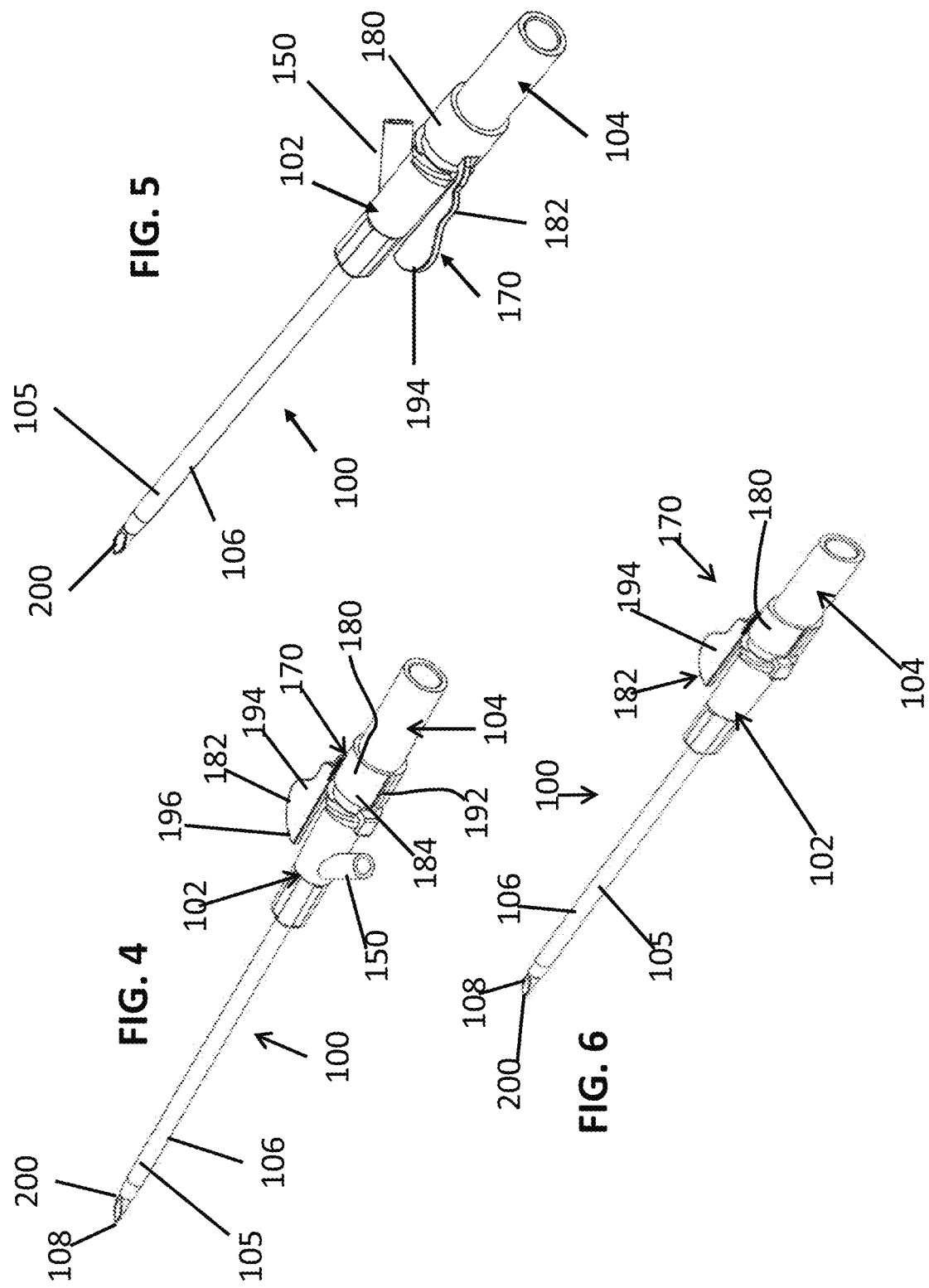

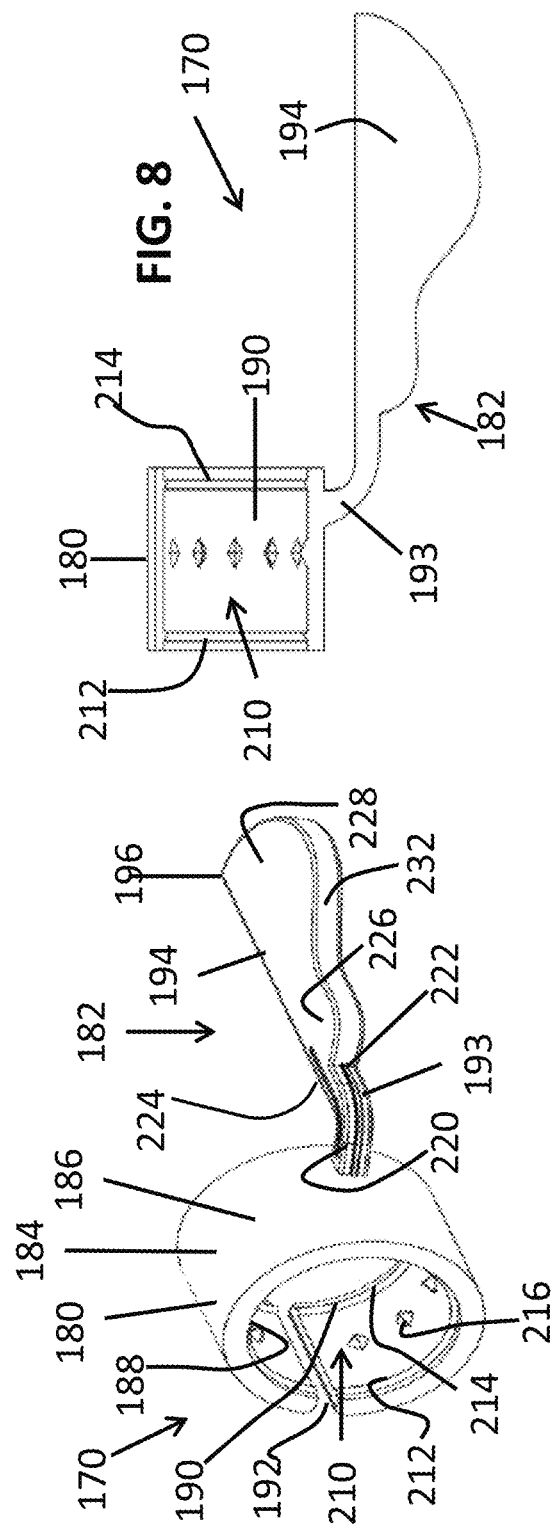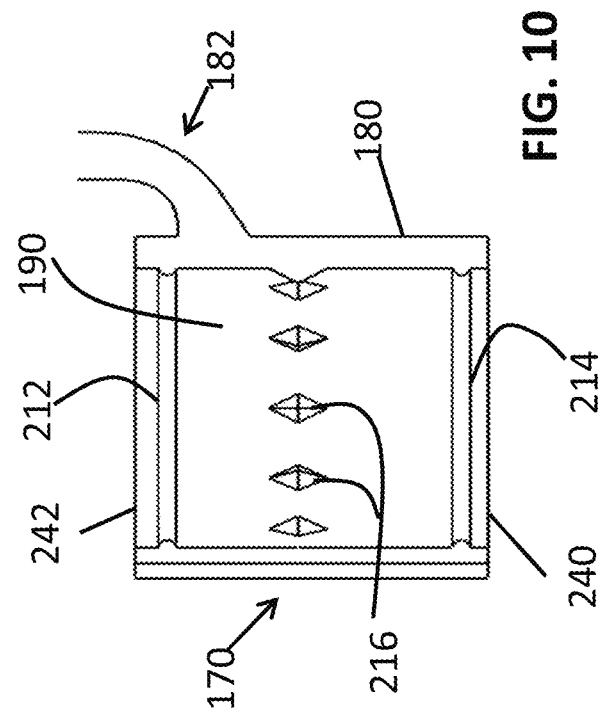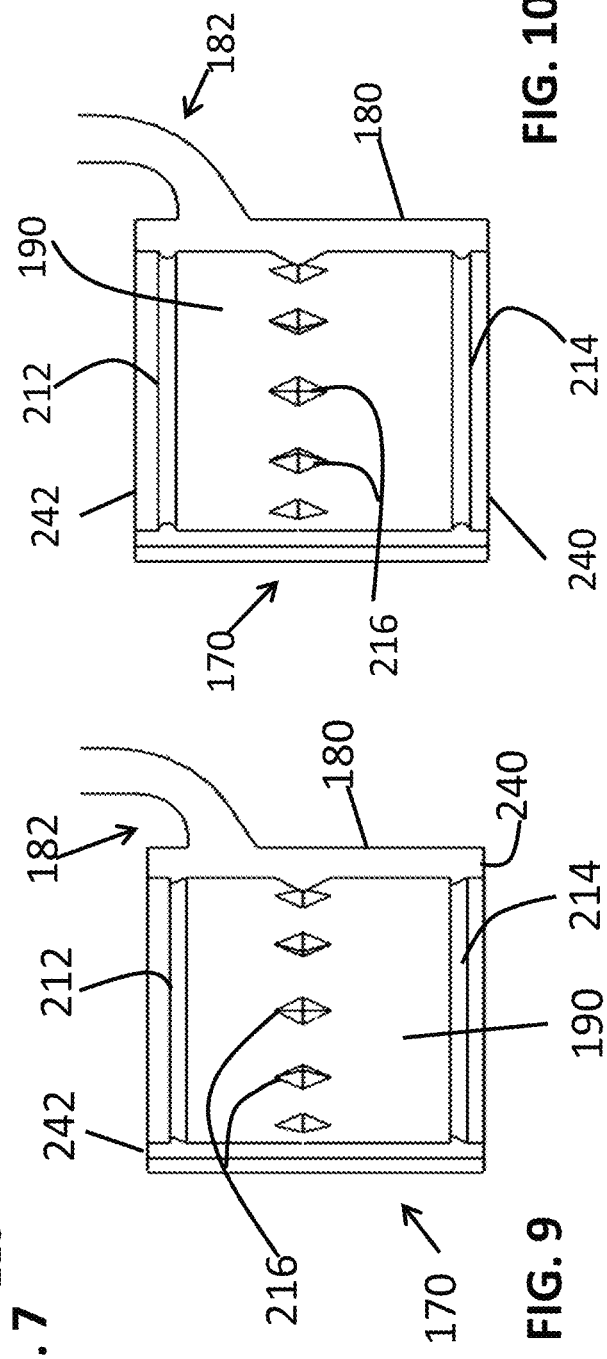

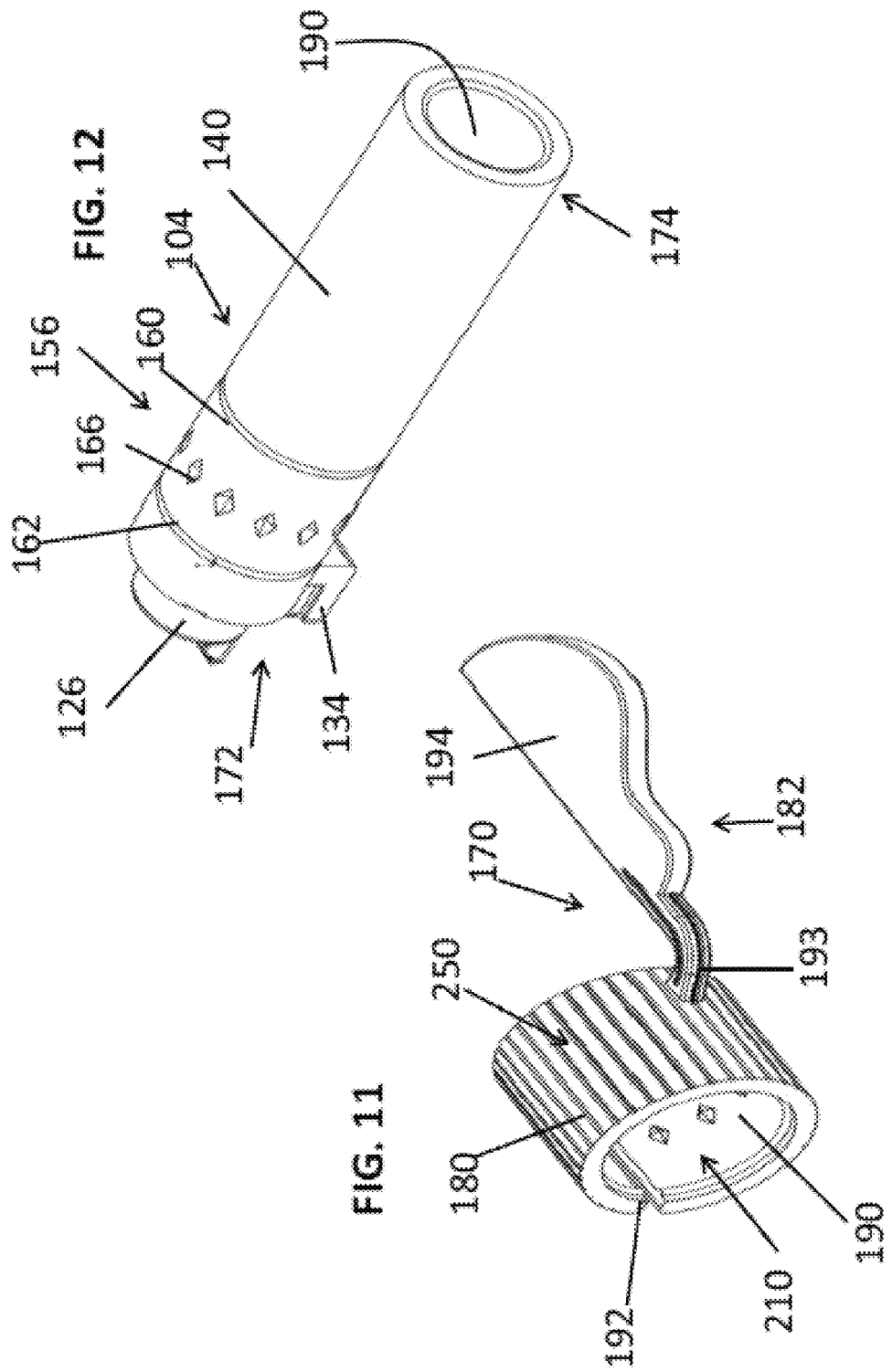

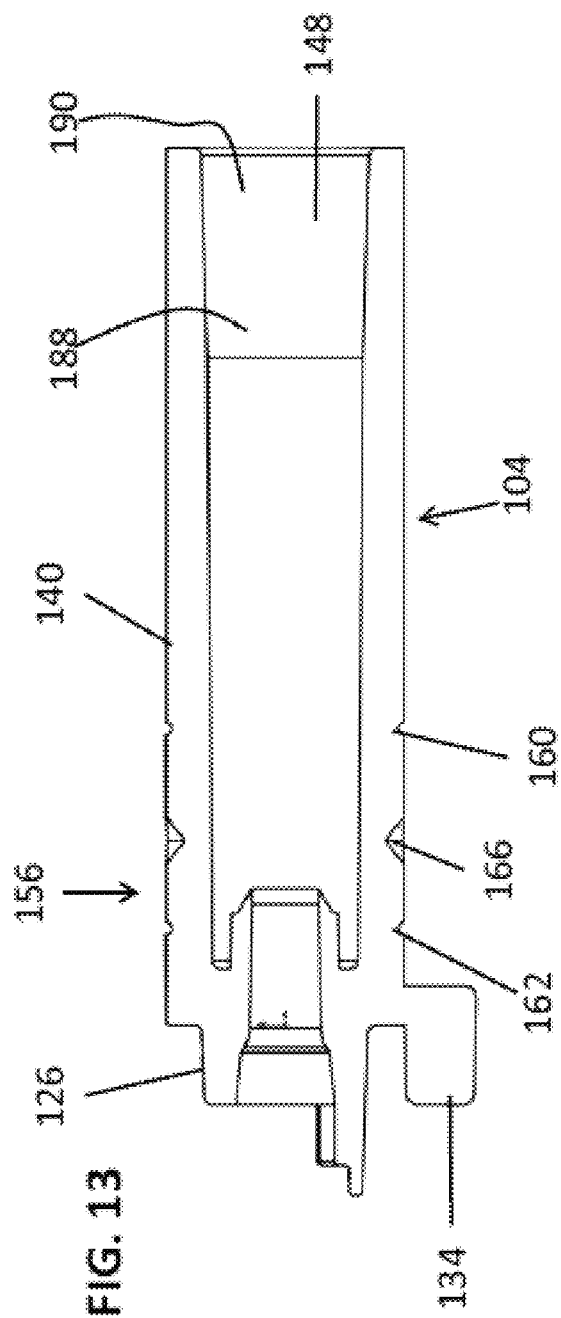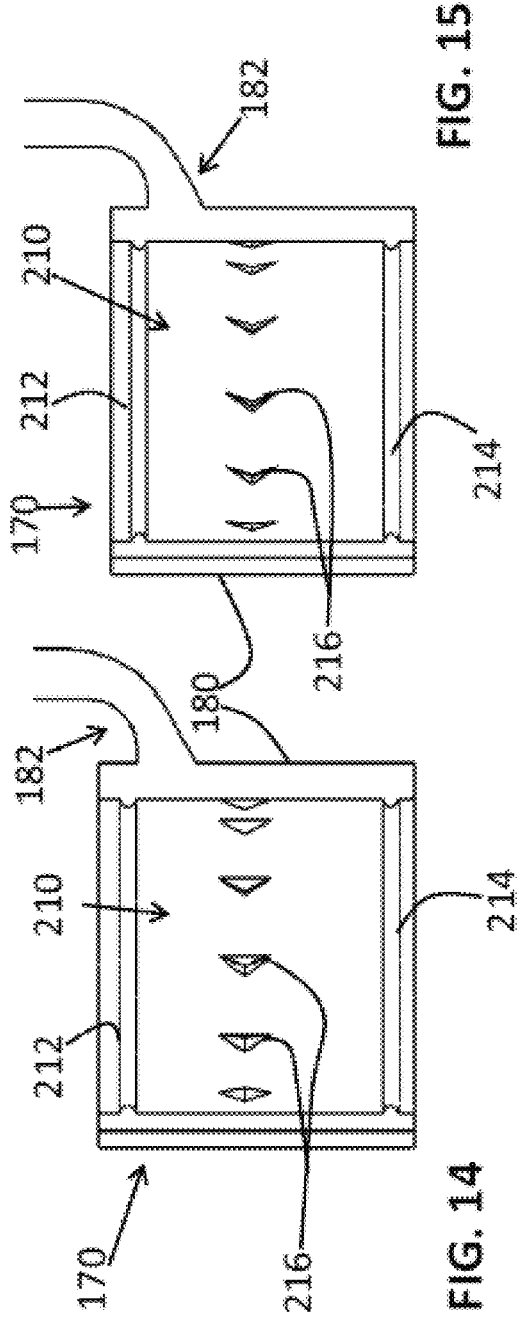

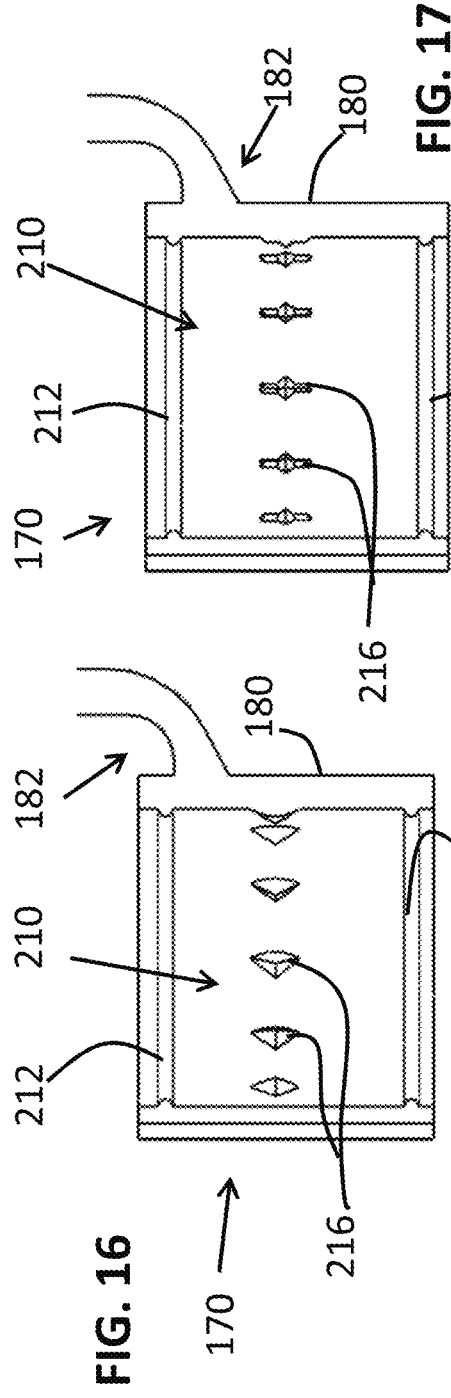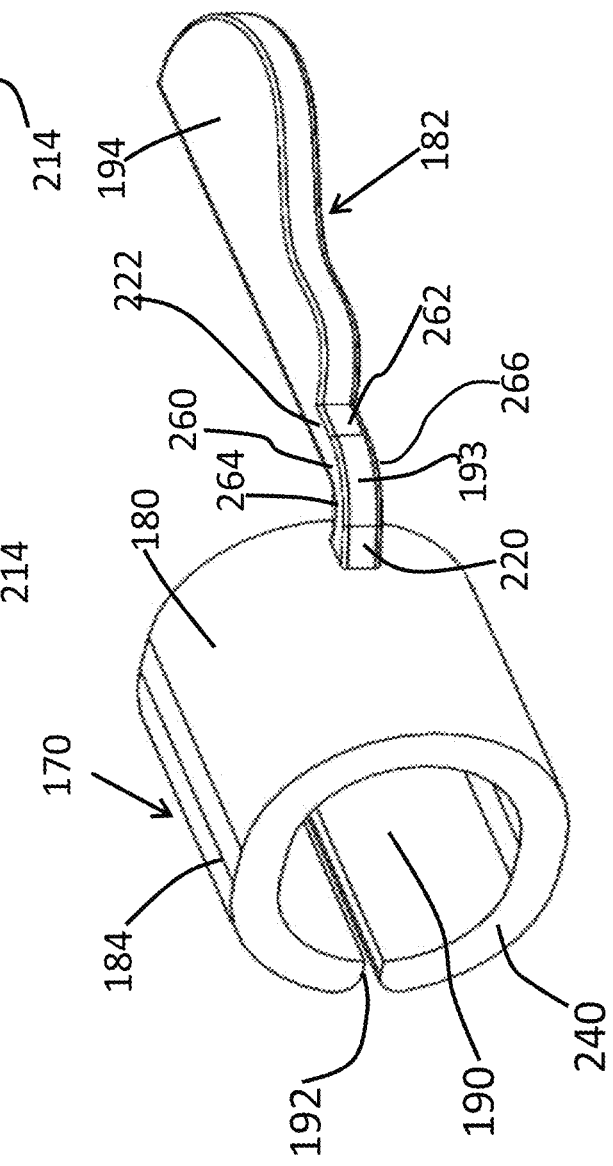

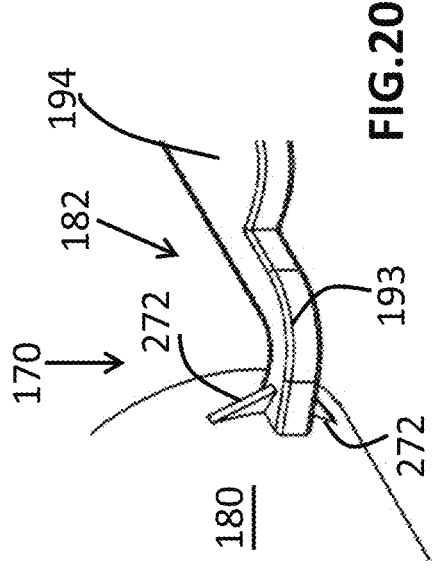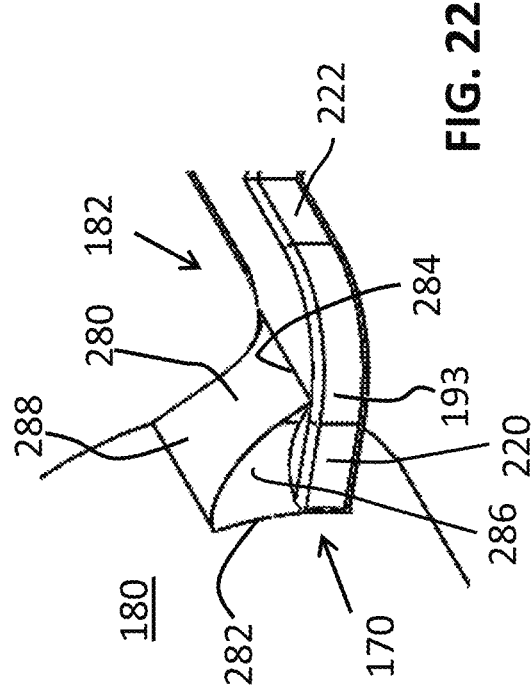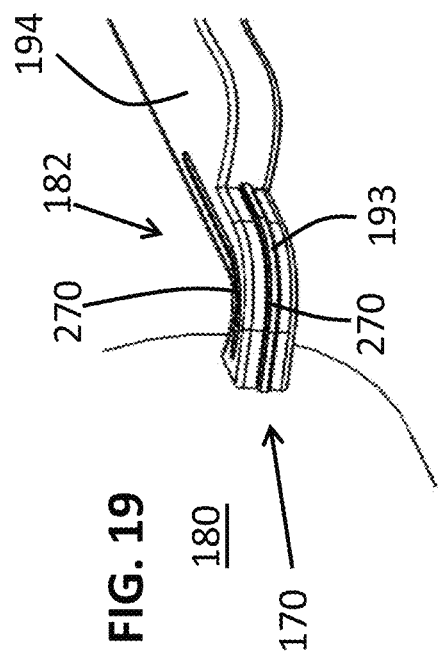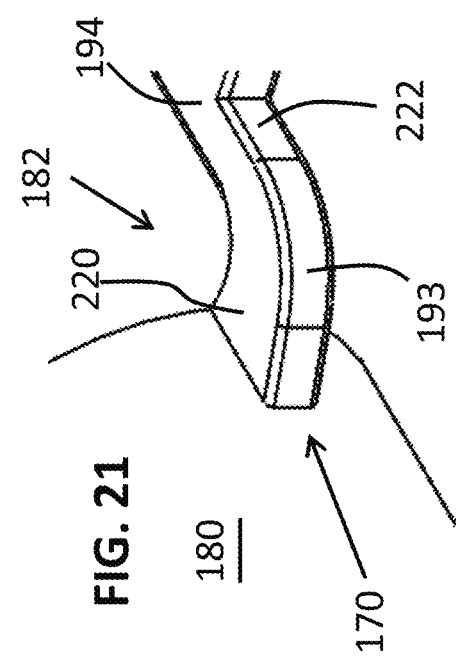

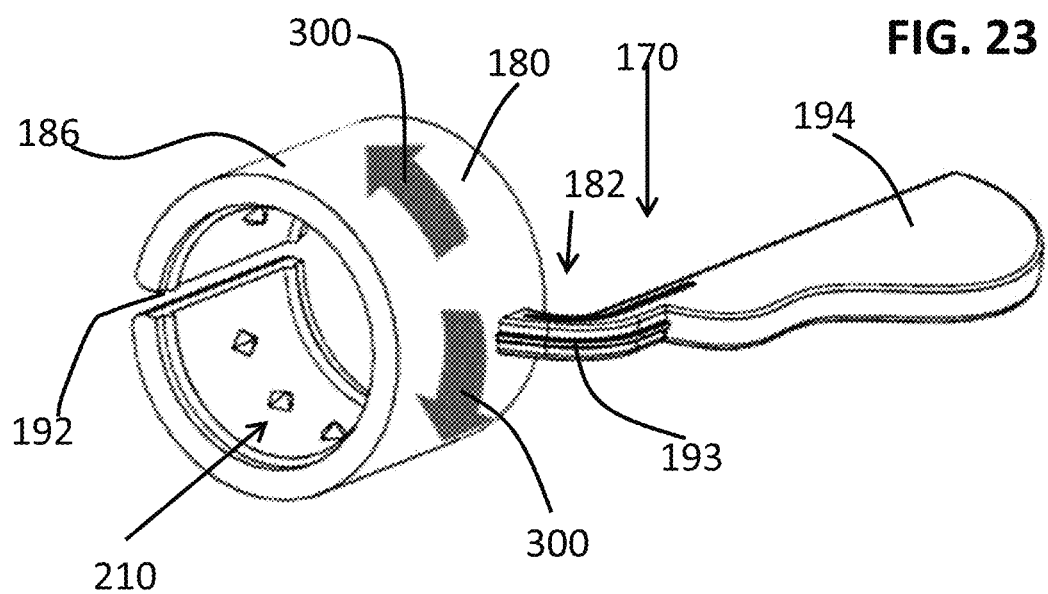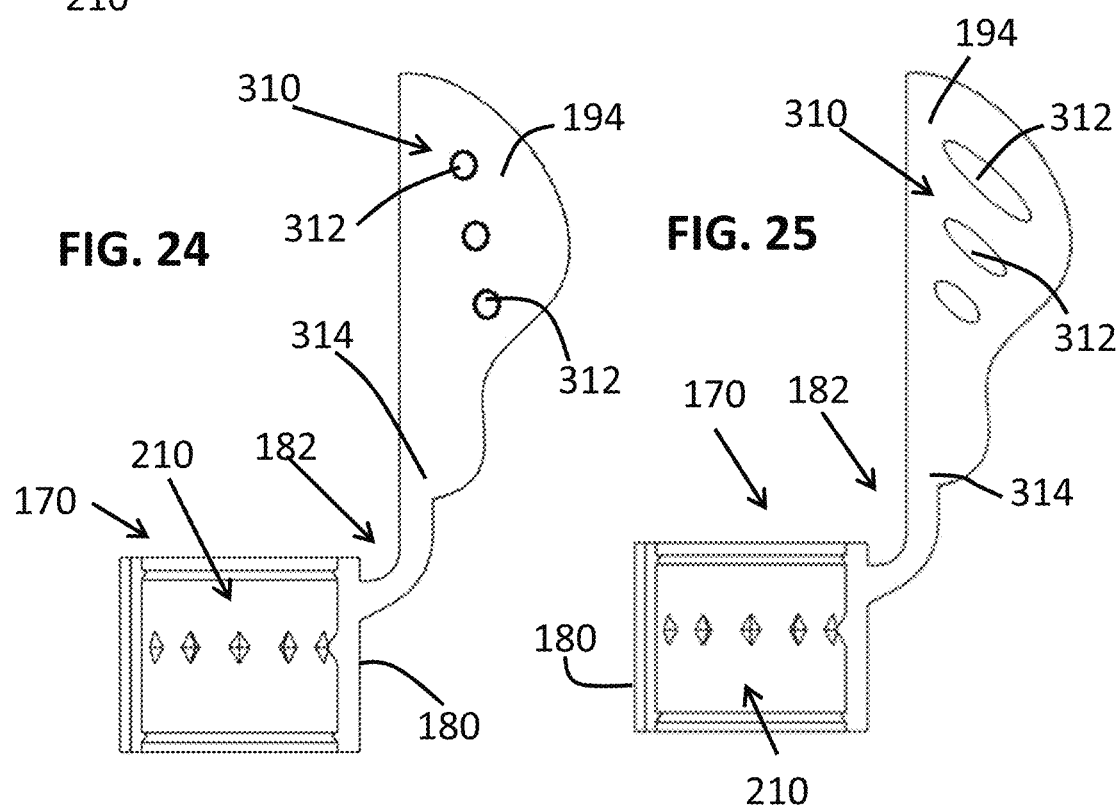

NEEDLE DEVICES WITH ADJUSTABLE GRIPS AND RELATED METHODS

FIELD OF ART

The disclosed invention generally relates to needle devices and more specifically to adjustable grips that can be added to needle devices to produce needle devices with adjustable grips and related methods.

BACKGROUND

Insertion procedure for an IV catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to slow down or stop the flow of blood through the catheter; and (4) the healthcare worker then tapes the exposed end of the catheter (the catheter hub) to the patient's skin and connects it to the source of the fluid to be administered into the patient's vein.

The problem is that immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. During the period between placing the used needle on a tray or a work station to the time it is discarded, the used needle is a potential source for disease transmissions for those that work near or around the needle.

Accordingly, exposed needle tips should be covered immediately following use to ensure greater worker safety. Ideally, the procedure for covering the needle tip should be passive, self-activating, or at least simple to perform. In addition, the device for covering the needle should be reliable and robust.

Needle devices often include safety systems that cover the tip of the needle to prevent accidental sticks after placement of the catheter tube into the vasculature of a patient. These systems can be either passive or active. In some systems, the safety features are located inside the catheter hub in the ready position while in other systems they are external of the catheter hub. In either location, the safety features serve the same function, to cover the needle tip in order to prevent accidental needle sticks after venipuncture.

SUMMARY

Aspects of the present disclosure include needle devices and related methods.

Exemplary needle assemblies of the present disclosure include a needle assembly comprising a first hub having a tubing extending therefrom, said tubing having a lumen and a distal opening and said first hub comprising a body comprising an exterior surface and an interior surface defining an interior cavity; a second hub having a needle extending therefrom, said needle comprising a needle tip with a needle bevel and said second hub comprising a body comprising an exterior surface with exterior surface mating features and an interior surface defining an interior cavity, said needle extending through the lumen with the needle tip extending distally of the distal opening of the tubing; an extension clip comprising a clip ring and a grip extension, said clip ring comprising a body comprising an exterior surface and an interior surface with interior surface mating features mounted around the exterior surface of the second hub, and said grip extension comprising a pad having a free end; and wherein the interior surface mating features of the clip ring mate with exterior surface mating features of the second hub and the pad is at a first angular position and wherein the clip ring is rotatable relative to the second hub to change an angular position of the pad to a second angular position.

Aspects of the present disclosure can further include a needle assembly comprising a first hub having a tubing extending therefrom, said tubing having a lumen and a distal opening; a second hub having a needle extending therefrom, said needle comprising a needle tip with a needle bevel and said second hub comprising a body comprising an exterior surface and an interior surface defining an interior cavity, said needle extending through the lumen with the needle tip extending distally of the distal opening of the tubing; an extension clip comprising a clip ring and a grip extension, said clip ring comprising a body comprising an exterior surface and an interior surface defining a bore mounted around the exterior surface of the second hub, and said grip extension comprising a pad having a free end, an inside edge, and an outside edge; and wherein the clip ring is rotatable relative to the second hub to change an angular position of the pad to a second angular position and wherein the free end points in a distal direction and the inside edge is spaced from the exterior surface of the second hub.

Yet further aspects of the present disclosure comprise a needle assembly comprising a needle hub comprising a body comprising an exterior surface and an interior surface defining an interior cavity, said needle hub having a needle with a needle tip and a needle bevel extending in a distal direction; exterior mating surface features formed on the exterior surface of the needle hub, said exterior mating surface features comprise a plurality of spaced apart exterior interference elements and at least one detent guide; an extension clip comprising a clip ring and a grip extension, said clip ring comprising a body comprising an exterior surface and an interior surface with interior surface mating features mounted around the exterior surface of the needle hub so that said interior surface mating features mate with said exterior mating surface features; where a pad of said grip extension is at a first angular position and wherein the clip ring is rotatable relative to the needle hub to change an angular position of the pad to a second angular position.

A needle guard can be located in the interior cavity of the first hub. The needle guard can comprise a proximal wall with an opening and at least one arm extending distally of the proximal wall. In some examples, two arms extend distally of the proximal wall with each arm comprising a distal wall. The two arms can intersect one another. In some examples, the needle guard can be located inside a third hub located between the first hub and the second hub.

A further feature of the present disclosure is a needle guard for use with a change in profile on the needle. In other examples, the needle guard can activate to cover the needle tip without a change in profile.

A tubing port can extend from a side of the first hub. Alternatively, a fluid port can extend from a side of the first hub.

The exterior surface mating features can comprise a detent guide. The detent guide can be a detent ring or a groove for receiving a detent ring.

The exterior surface mating features can comprise a plurality of spaced apart interference elements. The plurality of spaced apart interference elements can comprise a plurality of raised interference elements.

The plurality of spaced apart interference elements can alternatively comprise a plurality of recessed interference elements.

The exterior surface mating features can comprise a second detent guide.

The plurality of spaced apart interference elements can be located between the detent guide and the second detent guide.

The plurality of spaced apart interference elements can be spaced from one another by a gap that limits the pad to rotation in two-degree to forty five-degree increments. The mating interference elements can be arranged along an arc circle and spaced from one another by a gap, the distance between each pair of interference elements can control the range of angular movement of the pad as the pad and/or the clip ring rotates relative to the second hub.

The interior surface mating features of the clip ring can comprise a detent guide recessed from an edge opening of the clip ring.

The interior surface mating features of the clip ring can further comprise a second detent guide recessed from a second edge opening of the clip ring.

The clip ring can be rotatable relative to the second hub while the needle bevel remains at a twelve o'clock position.

The pad can be movable relative to the second hub and from a three o'clock position to a nine o'clock position.

The grip extension of the extension clip can further comprise a connection branch connected to an exterior of the clip ring. The connection branch can comprise a first section extending from the clip ring and a second section connected to the pad of the grip extension.

The first section and the second section of the connection branch can have the same cross-section.

The first section of the connection branch can have a larger cross-sectional dimension than a cross-sectional dimension of the second section.

One or more ribs can extend from a surface of the connection branch.

A flange tab can attach to the clip ring and the connection branch.

An anchor can attach to the clip ring and the connection branch.

Exterior gripping features can be included on the exterior surface of the clip ring. The gripping features can comprise raised projections or bumps.

Rotation instructions can be included on the exterior surface of the clip ring. The rotation instructions can comprise an arrow. In some examples, the instructions can comprise two arrows pointing in two different directions.

The interior surface mating features of the clip ring can comprise two spaced apart raised detent rings and a plurality of raised interior interference elements. The raised interior interference elements each can comprise a square shape, an octagon shape, an asscher shape, a cushion shape, an emerald shape, a heart shape, a marquise shape, an oval shape, a pearl shape, a princess shape, a radiant shape, a round shape, a drop shape, a ball shape, a baguette shape, a mine shape, a rose shape, a trillion shape or a gear shape.

The gear shape can comprise herringbone gear teeth or spur gear teeth.

The two spaced apart raised detent rings of the clip ring can each comprise a semi-spherical cross section, a square cross-section, a triangle cross-section, or a right triangle cross-section.

The pad of the grip extension can comprise a first surface and an opposed second surface and wherein a plurality of gripping features can be incorporated with the first surface, the second surface, or both. The gripping features can comprise a plurality of raised bumps or elongated oval bumps.

A still further aspect of the present disclosure is a method of manufacturing a needle assembly. The method can comprise: forming a first hub with a tubing extending therefrom, said tubing having a lumen and a distal opening; forming a second hub with a needle extending therefrom, said needle comprising a needle tip with a needle bevel and said second hub comprising a body comprising an exterior surface and an interior surface defining an interior cavity, said needle extending through the lumen with the needle tip extending distally of the distal opening of the tubing; placing a clip ring of an extension clip around the exterior surface of the second hub and orientating a free end of a pad of a grip extension in a distal direction and an inside edge of the pad spaced from the exterior surface of the second hub; and providing interior interference elements in a bore of the clip ring for mating with exterior interference elements on the exterior surface of the second hub.

Aspects of the present disclosure further include an extension clip for use with a needle device, such as a needle hub of the needle device. The extension clip can include a grip ring and a grip extension. The grip ring can comprise a body comprising an exterior surface and an interior surface defining a bore having two open ends and a slit. Interior surface mating features can be provided in the bore. The interior surface features can include two detent guides and a plurality of interior interference elements. Gripping features can be incorporated with the exterior surface of the clip ring. Rotation directions or instructions can be incorporated with the exterior surface of the clip ring. The directions or instructions can comprise an arrow or two arrow pointing in two different directions.

BRIEF DESCRIPTION OF THE DRAWINGS

These and other features and advantages of the present devices, systems, and methods will become appreciated as the same becomes better understood with reference to the specification, claims and appended drawings wherein:

FIG. 2 is a perspective view of the needle assembly of FIG. 1 and wherein the first hub is shown with a tubing port.

FIG. 3 is a perspective view of a second hub, if used with a first hub otherwise a needle hub, with a needle and an extension clip aligned for mounting onto the second hub.

FIG. 4 is a perspective view of the needle assembly of FIG. 2 with an extension clip having a pad positioned at a three o'clock position.

FIG. 5 is a perspective view of the needle assembly of FIG. 4 and wherein the pad is rotated to a nine o'clock position.

FIG. 6 is a perspective view of a needle assembly with an extension clip having a pad positioned at a three o'clock position and wherein the first hub is without a tubing port, otherwise called a standard catheter hub.

FIG. 7 is a perspective view of an extension clip provided in accordance with aspects of the present disclosure.

FIG. 8 is a cross-sectional side view of the extension clip of FIG. 7 taken along a plane defined by the slit and the tab of FIG. 7.

FIG. 9 is a partial cross-sectional side view of an alternative extension clip provided in accordance with further aspects of the present disclosure.

FIG. 10 is a partial cross-sectional side view of another alternative extension clip provided in accordance with further aspects of the present disclosure.

FIG. 11 is a perspective view of an alternative extension clip provided in accordance with further aspects of the present disclosure.

FIG. 12 is a perspective view of needle hub provided in accordance with aspects of the present disclosure.

FIG. 13 is a cross-sectional side view of the needle hub of FIG. 12.

FIG. 14 is a partial cross-sectional side view of another alternative extension clip provided in accordance with further aspects of the present disclosure.

FIG. 15 is a partial cross-sectional side view of yet another alternative extension clip provided in accordance with further aspects of the present disclosure.

FIG. 16 is a partial cross-sectional side view of still yet another alternative extension clip provided in accordance with further aspects of the present disclosure.

FIG. 17 is a partial cross-sectional side view of yet another alternative extension clip provided in accordance with further aspects of the present disclosure.

FIG. 18 is a perspective view of an extension clip provided in accordance with aspects of the present disclosure.

FIG. 19 is a partial perspective view of another alternative extension clip provided in accordance with further aspects of the present disclosure.

FIG. 20 is a partial perspective view of yet another alternative extension clip provided in accordance with further aspects of the present disclosure.

FIG. 21 is a partial perspective view of still yet another alternative extension clip provided in accordance with further aspects of the present disclosure.

FIG. 22 is a partial perspective view of yet another alternative extension clip provided in accordance with further aspects of the present disclosure.

FIG. 23 is a perspective view of an alternative extension clip provided in accordance with aspects of the present disclosure.

FIG. 24 is a partial perspective view of another alternative extension clip provided in accordance with further aspects of the present disclosure.

FIG. 25 is a partial perspective view of yet another alternative extension clip provided in accordance with further aspects of the present disclosure.

DETAILED DESCRIPTION

Figure 1:
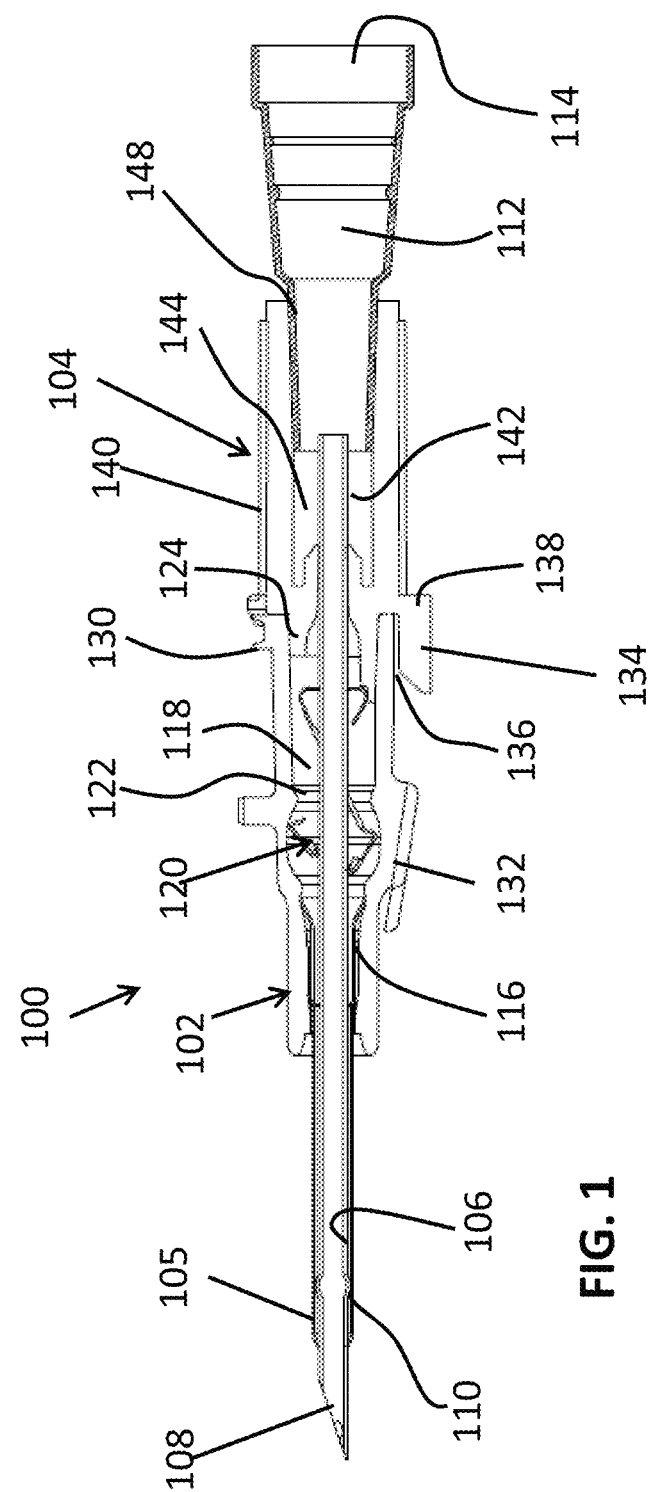
FIG. 1 is a schematic cross-sectional side view of a needle assembly having a first hub removably connected to a second hub.

The detailed description set forth below in connection with the appended drawings is intended as a description of the presently preferred embodiments of needle devices provided in accordance with aspects of the present assemblies, systems, and methods and is not intended to represent the only forms in which the present devices, systems, and methods may be constructed or utilized. The description sets forth the features and the steps for constructing and using the embodiments of the present assemblies, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

With reference now to FIG. 1, a cross-sectional side view of a needle assembly 100 provided in accordance with aspects of the present disclosure is shown, which comprises a first hub 102 having an over-the-needle tube or tubing 105 attached thereto and a second hub 104 having a needle 106 attached thereto. The tubing 105 has a lumen or bore for receiving the needle and has a distal opening or distal end opening. The needle assembly 100 can be called a catheter assembly or a catheter device. The needle 106 has a needle tip 108 and can include a change in profile 110 located proximal of the tip 108 for use with a needle guard. The needle tip 108 extends distally of the distal end opening of the tube or tubing 105 in the ready to use position with the change in profile 110, if incorporated for use with a needle guard, located proximally of the distal tube opening. The change in profile 110 can be a crimp, a bump, or a material build-up having different profile than other diameter sections of the needle shaft. As used herein, the term proximal is understood to mean an end or side closer to the practitioner and the term distal is the opposite end or side.

The change in profile 110 can be used to interact with a needle guard during retraction of the needle, as further discussed below. The first hub 102 may alternatively be referred to as a catheter hub and the second hub 104 may alternatively be referred to as a needle hub. A vent plug 112 is disposed at the proximal open end 148 of the second hub 104 and has a vent filter 114 at a proximal end thereof, which is conventional. As shown, the tube 105 is attached to the first hub 102 by a ferrule 116 and may be referred to as a catheter tube.

A needle guard 120 can optionally be provided in the interior cavity 118 of the first hub 102 for covering the needle tip 108 in the protective position. When incorporated, the needle guard 120 can be one of the needle guards disclosed in U.S. Pat. No. 6,616,630, the contents of which are expressly incorporated herein by reference. In some examples, the needle guard 120 can be omitted. If so, the change in profile can also be omitted. In still other examples, a needle guard can be included without also including a change in profile on the needle. In yet other examples, the needle guard 120 can be located in a third housing between the first hub and the second hub. An exemplary needle guard located in a third housing is disclosed in U.S. Pat. No. 8,597,249, the contents of which are expressly incorporated herein by reference.

The needle guard 120 can include a proximal wall and two arms extending distally of the proximal wall. The two arms can intersect one another in the ready to use position of FIG. 1 and in the protective position in which the needle guard covers the needle tip, and as viewed from a side. In some examples, the two arms of the needle guard 120 can extend in a distal direction without intersecting one another. Two distal walls, one on each arm, can be incorporated to block the needle tip. The two distal walls are biased outwardly by the needle 106 in the ready to use position of FIG. 1 and disposed distally of an internal change in profile 122 inside the first hub 102 in the ready to use position. The internal change in profile 122 can be a reduced diameter section located next to an inside diameter section of a larger dimension. Each distal wall can include a curved lip to facilitate relative movement between the needle guard and the needle. When in the ready to use position, the dimension measured between the two joints at each arm, at the intersection between each arm and its respective distal wall, is larger than the inside diameter of the internal change in profile 122, which prevents the needle guard 120 from moving proximally thereof. Once the needle tip moves proximally of the two distal walls, the two arms are allowed to move radially inward and one or both distal walls close over the needle tip to block the needle tip in a protective position. At that point, the dimension between the two joints decreases and is smaller than the internal dimension of the internal change in profile 122, which then allows the needle guard to move proximally and be removed from the catheter hub with the needle.

The first hub 102 has a proximal opening 124 having a nose section 126 of the second hub 104 disposed therein. The proximal opening 124 has a female Luer for receiving a male Luer tip, such as a syringe, an IV tubing adaptor, a Luer extension, etc. External threads 130 can be provided on the exterior surface at the proximal end for threaded engagement with a threaded collar of a male Luer tip. A pair of stabilizing wings 132 can extend radially of the first hub to facilitate securement or anchoring of the first hub 102 to a patient following successful venipuncture. Optionally the wings can be omitted. The first hub 102 can embody a standard IV catheter hub without a tubing port. In other examples, the first hub can include a tubing port. In still other examples, the first hub 102 can include a side fluid port, also known as a ported catheter.

The first hub 102 is removably secured to the second hub 104 by receiving the nose section 126 of the second hub in the proximal opening 124 thereof. A flange or extension 134 is provided on the second hub 104 and together with the nose section 126 define a gap 136 having part of the first hub located therein. Optionally the flange or extension 134 can be omitted and a stub 138 or other surface mating features provided. The stub 138 can limit the extent of insertion of the second hub 104 into the first hub 102. A rib or annular flange can also extend from the nose section 126 of the second hub 104 to limit the extent of insertion of the nose section into the first hub. The stub 138 can be an optional structural features as a clinician or practitioner can rotate the tubing port 150 according to their preference, especially for left hand application, and omitting the stub can facilitate to rotation.

The second hub 104 has a body 140 having an interior cavity 144 having the proximal end 142 of the needle 106 projecting there-into. The interior cavity 144 can function as a primary blood flashback chamber. The proximal opening 148 of the body 140 can have a female Luer for receiving a vent plug therein and the exterior can have threads or be without threads. In an example, the exterior of the body 140 of the second hub 104 is generally cylindrical and without threads for receiving an adjustable grip or extension clip, as further discussed below. The first and second hubs can be made from plastic materials, such as by plastic injection. The body of second hub 104 may have some ergonomics grips or curvature for users who do not require a clip ring. For products that incorporate an extension ring, as further discussed below, the ergonomics grips or curvature on the cannula hub might also be useful when the clinician is rotating the extension ring to their desired angle. One hand can be used to hold on the ergonomics grip or curvature of the cannula hub while the second or other hand can hold on to the extension grip 182 or extension ring 170 to rotate.

With reference now to FIG. 2, an isometric view of the needle assembly 100 of FIG. 1 is shown. The present needle assembly 100 is shown with a side tubing port 150, which can be connected to a plastic tubing and the plastic tubing having a tubing clamp and a needleless valve (not shown). In other examples, such as shown in FIG. 6, the needle assembly can have a standard catheter hub without a side tubing port. The exterior surface 154 of the body 140 of the second hub 104 is shown with surface mating features 156 for interacting with an extension clip 170, as further discussed below. In other examples, a second fluid port can be included with the first hub 102 for use to add fluids, such as medicinal fluids, into first hub 102. When incorporated, the first hub 102 may be referred to as a ported catheter. The second port can have a female Luer for receiving a male Luer tip. The proximal opening of the second hub 104 is shown without a vent plug but can be included.

With reference now to FIG. 3, the second hub 104 with a needle 106 is shown without a first hub. The second hub 104 can be the same as that of FIG. 2. The needle 106 is also shown without a change in profile proximal of the needle tip 108, which can alternatively be incorporated when the needle assembly of FIG. 2 incorporates a needle guard, unless the needle guard does not require interaction with a change in profile is used in which case no change in profile is needed.

The body 140 of the second hub 104 is shown with surface mating features 156, which in the embodiment shown include a first detent guide 160, a second detent guide 162, and a plurality of spaced apart interference elements 166. In an example, the plurality of interference elements 166 are located between the first detent guide 160 and the second detent guide 162. In other examples, the first and second detent guides 160, 162 can be located adjacent one another and the plurality of interference elements 166 can be located adjacent the first detent guide 160 or the second detent guide 162. The two detent guides 160, 162 can each embody a raised projection guide, a recessed guide, or one of each. The detent guides 160, 162 can form around the external periphery of the second hub 104, continuously or otherwise. Thus, in some examples, the first and second detent guides can embody raised projection rings or recessed rings. The plurality of interference elements 166 can embody raised surfaces, such as raised embossed surfaces, or recessed surfaces.

The surface mating features 156 are configured to mate with corresponding surface mating features of an extension ring 170 to enable the clip ring 180 (FIG. 7) of the extension ring to attach thereto and rotate to allow the pad to change from a first angular position to a second angular position. In some examples, only the first detent guide 160 or the second detent guide 162 is incorporated with the second hub but not both. In other examples, more than two detent guides are incorporated with the second hub 104.

The plurality of interference elements 166 can be evenly spaced around the outer periphery of the body 140 and can number between six to sixty elements. In other examples, the number of interference elements can be higher and not evenly spaced around the outer periphery. In general, the higher the number of interference elements, the greater the precision for angular rotation the extension clip or extension ring 170, as further discussed below. In some examples, fourteen to sixty interference elements 166 are provided for interacting with fourteen to sixty corresponding mating interference elements on the extension clip or ring 170. For example, when the extension clip 170 is rotated, the interior interference elements on the extension clip 170 are rotated relative the external interference elements 166 on the second hub 104 until the rotation stops and the two sets of interference elements engage. A rotational movement from one interference element to the next as the collar on the extension clip rotates relative to the second hub can represent a movement of a degree or more along an arc circle, which can be determined by the size and the spacing of the plurality of interference elements.

The number of interference elements of the extension clip 170 and the number of interference elements of the second hub 104 may not be the same. For example, the number of external interference elements 166 can be more or greater than the interior interference elements 216. In other examples, the number of external interference elements 166 can be less than the interior interference elements 216. The different numbers can be selected to reduce the number of mating interference elements that must be overcome during rotation of the extension clip or ring 170 relative to the second hub 104. The different numbers of interference elements selected for the extension clip and the second hub can lead to lower rotational force during rotation of the extension clip or ring 170 relative to the second hub 104 but provides precise control of the radial position.

The plurality of interference elements 166 can embody raised surfaces, such as raised embossed surfaces, or recessed surfaces as previously discussed. If the interference elements 166 are raised surfaces, then the corresponding mating interference elements on the extension clip 170 are recessed surfaces for mating the two sets of interference elements together. If the interference elements 166 are recessed surfaces, then the corresponding mating interference elements on the extension clip or ring 170 are raised surfaces for mating the two sets of interference elements together. In some examples, the inference elements 166 on the second hub 104 and the interference elements on the extension clip 170 can have both raised and recessed surface mating features.

The surface mating features 156 can be incorporated on the body 140 of the second hub 104 closer to the distal end 172 than the proximal end 174 of the body. In some examples, the surface mating features 156 are located approximately half-way between the proximal end and the distal end. In still other examples, the surface mating features 156 can be incorporated on the body 140 closer to the proximal end 174 than the distal end 172.

The extension clip 170 is shown with a clip ring 180 and a grip extension 182 extending from the clip ring 180. The extension clip 170 can be molded from any number of plastic materials. In an example, the clip ring 180 comprises a body 184, which can be elongated and cylindrical or generally cylindrical, with an exterior surface 186 and an interior surface 188 defining a bore 190. In other examples, the bore and/or external profile of the body 184 are other than cylindrical. A slit or slot 192 can be provided along a lengthwise direction of the body 184 through the wall of the body 184, between and through both proximal and distal edges 240, 242 (FIG. 9) of the body 184 so that the slit is provided along the entire length of the body 184.

The slit 192 can be provided to allow the body 184 to expand for mounting onto the body 140 of the second hub 104. In other examples, the body 184 of the clip ring 180 can be without a slit 192 and the bore 190 can be sized to readily mount or slide over the body 140 of the second hub 104. In this alternative embodiment without a slit, a gasket or pliable pad or ring can be provided between the interior surface 188 of the clip ring 180 and the exterior surface of the body 140 of the second hub 104 to enable interference or frictional engagement so that the clip ring 180 can rotate and settle to a desired angular position. For example, a rubber band sized with an appropriate width, thickness, ID, and OD can be used as a bushing between the clip ring 180 and the second hub 104 to enable rotation and retention of the clip ring 180. In still other examples, the clip ring 180 can be made from a pliable material, such as from a rubber material, which can stretch and be mounted onto the second hub 104 without a slit.

The grip extension 182 can have a connection branch 193 (FIG. 7) attached to the exterior surface 186 of the clip ring 180 and a pad 194 extending from the connection branch 193. The pad 194 can have a free end 196 (FIG. 7), which is understood to be free from any connection or attachment, extending in a proximal direction or a distal direction depending on the direction of mounting of the extension clip 170 onto the second hub 104. The extension clip 170 can be attached to the body 140 of the second hub 104 by sliding one of the open ends of the clip ring 180 onto the exterior of the body 140 in the direction of the insertion arrow shown in FIG. 3. As shown, the orientation of the extension clip or ring 170 can be arranged or selected so that the free end 196 of the pad 194 points in the distal direction. In other examples, the extension clip can be mounted so that the free end 196 can point in the proximal direction. The clip ring 180 is slid onto the body 140 of the second hub 104 until the interior surface mating features inside the bore 190 of the clip ring 180 engage the surface mating features 156 of the second hub 104.

The angular position of the pad 194 of the extension clip 170 with the axis of the needle 106 as the center of rotation can be adjustable. In an example, the angular position of the pad 194 can be adjusted while fixing the position of the bevel 200 of the needle tip 108 so that it faces up, as shown in FIG. 3, which can be labeled as roughly the twelve o'clock position. The angle of rotation of the pad 194 can vary from zero to 360 degrees, in two to forty-five degree increments. In an example, the pad can be rotated in 4-degree to 15-degree increments. In other examples, the pad 194 can be rotated in ninety degree increments only. The increments can vary depending on the number of external interference elements 166 incorporated with the second hub 104 and the internal interference elements incorporated with the clip ring 180. The pad 194 can also be rotated to an angular position in which the interference elements in the interior of the clip ring 180 and the second hub 104 do not engage, such as between full engagement of the interference elements. However, doing so can cause unwanted residual rotation during use. The zero position or angle of the pad 194 can be any arbitrary reference point and the rotational movement based on said reference point. For example, the pad 194 being at the three o'clock position can be considered the zero position and a ninety degree rotation therefrom in the clockwise direction will put the pad 194 at the six o'clock position. Thus, the pad 194 can rotate from a first angular position to a second angular position by rotating the clip ring relative to the second hub. The extension clip 170 can be mounted onto the second hub 104 with the needle 106 removed from the tube 105 as shown in FIG. 3 or with the second hub 104 engaged to the first hub 102, as shown in FIG. 2. The extension ring 170 can also be pre-mounted in the position of 1 o'clock towards the zero position, depending on the packaging space or space for the index finger to be gripping at the pad 194. This can provide the convenience to most of the clinicians to exclude any rotational steps for catheter insertion.

In some examples, a first needle assembly 100 and a second needle assembly 100 are formed, which can be similar or substantially identical. The needle assemblies can both resemble the needle assembly 100 of FIG. 2 with a side tubing port 150 or the needle assembly 100 of FIG. 6 without any side tubing port. The two needle assemblies can alternatively be formed with a side fluid port or formed as ported catheters. An extension clip 170 is then added to the first needle assembly 100 but not to the second needle assembly 100. This allows two similar needle assemblies to be manufactured using the same manufacturing tools and methods, such as the same molds at the same assembly line, but wherein the first and second needle assemblies can be marketed or sold to different markets or regions. For example, a first country or region may prefer to use a needle assembly 100 with a grip extension while a second country or region may prefer to use a needle assembly 100 without a grip extension. By incorporating an extension clip 170 of the present disclosure onto one of two similar needle assemblies, the two similar needle assemblies can be used in two different regions, one with a grip and one without a grip. In some examples, all needle assemblies are provided with the extension clips of the present disclosure and the users are given the option to remove the extension clips. In yet other examples, similar needle assemblies with and without the extensions clips are provided to the same market, hospital, or region and the users have the option to select which needle assembly to use.

An additional aspect of the present disclosure is a needle hub comprising a body comprising an exterior surface and an interior surface defining a bore, said needle hub having a needle with a needle tip and a needle bevel extending in a distal direction. The exterior surface of the body comprises exterior mating surface features. The exterior surface mating features can comprise a plurality of spaced apart exterior interference elements. In some examples, the exterior surface mating features can include at least one detent guide. In other examples, the exterior surface mating features can include a second detent guide. The plurality of spaced apart exterior interference elements can locate between the two detent guides or to one side of both of the detent guides. The needle hub with the exterior surface features is usable with any one of the extension clips described elsewhere herein. The pad on the extension clip usable with the needle hub is rotatable from a first angular position to a second angular position. A free end of the pad can extend in a distal direction or a proximal direction and an inside edge of the pad can be spaced from the exterior surface of the needle hub. Said extension clip and said needle hub can interact in similar manner as second hubs and extension clips discussed elsewhere herein.

FIG. 4 shows a needle assembly 100, such as the ones shown in FIGS. 1 and 2, having an extension clip 170 attached thereto with the free end 196 of the grip extension 182 pointing in the distal direction. The extension clip or extension ring 170 is pushed in the distal direction along the installation arrow direction (FIG. 3) until the interior surface mating features of the clip ring 180 engage the exterior surface mating features 156 of the second hub 104. In an example, the surface mating features of the clip ring 180 engage two detent guides 160, 162 on the second hub and a plurality of raised interference elements on the clip ring 180 engage a plurality of recessed interference elements 166 on the second hub. In another example, the surface mating features of the clip ring 180 engage two detent guides 160, 162 on the second hub and a plurality recessed interference elements on the clip ring 180 engage a plurality of raised interference elements 166 on the second hub.

The angular position of the pad 194 is shown at a three o'clock position looking in the distal direction from the proximal end, which can be labeled or identified as the zero position with the needle bevel 200 of the needle tip 108 facing up. The pad 194 can be rotated in the clockwise or counter-clockwise direction from the zero position to change its angular position while leaving the needle bevel 200 in essentially the same upward position. Additionally or alternatively, as the pad 194 is rotated in the clockwise or counter-clockwise direction, the first hub 102 can be rotated relative to the second hub 104 to change the angular position of the tubing port 150. As shown, the tubing port 150 is at roughly the nine o'clock position, looking in the distal direction from the proximal end. In an example, the pad 194 is rotated relative to the second hub 104. For example, the second hub 104 can be fixed from rotation to fix the needle bevel position while the pad 194 is rotated relative to the second hub 104 to a desired angular position allowed by the assembly for use by the practitioner. A rotational control extension ring or a limiting structure can be also used to limit the rotational angle of the extension ring 170. This rotational control feature or limiting feature can prevent unnecessary action, such as over-rotation, when the extension clip 170 is rotated below a plane defined by the bevel. A ring detent can be replaced with a screw type detent. A screw type detent can limit the rotation of the extension clip from a zero position of 3 o'clock counterclockwise to 9 o'clock and reverse, from the 9 o'clock clockwise to the 3 o'clock. The clinician can be restricted from further rotating beyond this range or angle. The rotation can include the interference elements to precisely control the radial position, while preventing the ring from "over" rotating outside of a desired range. In this alternative embodiment, the interference elements of both surfaces can have different size and shape, depending on the screw pitch.

Thus, for a left-handed user, for example, the needle assemblies of the present disclosure allow the pad 194 of the grip extension 182 to be rotated 180 degrees to the nine o'clock position and the tubing to be rotated 180 degrees to the three o'clock position while holding the second hub 104 steady to maintain the needle bevel 200 in the upward or twelve o'clock position. In other examples, the grip extension and the tubing port can be rotated along a different arc length or value, such as some angular value less than 180 degrees or larger than 180 degrees. For the same-handed user, either left-handed (LH) or right-handed (RH) user, the pad 194 can also be rotated to an angular position that is more comfortable or useful for the particular user. For example, a first RH-user likes the pad 194 to be at a two o'clock position while second RH-user likes the pad to be at a one o'clock position. The needle assemblies 100 and extension clips 170 with grip extensions 182 of the present disclosure can allow the pad 194 to be rotated to the desired angular position without having to resort to specifically made needle assemblies with fixed pad 194 positions. For a manufacturer of needle assemblies, the same production line or mold assemblies can be used to mass produce needle assemblies that can then optionally be modified to include grip pads and wherein the grip pads can be adjusted to different angular positions relative to the needle bevel position. While less preferred, the second hub 104 can also be rotated so that the needle bevel 200 is at an angular position other than the twelve o'clock. It is normally more preferred but not required to have the needle bevel 200 at the twelve o'clock position while the pad 194 is rotated relative to the second hub or needle hub 104 to a desired angular position.

FIG. 5 shows the needle assembly 100 and the extension clip 170 of FIG. 4 with the first hub 102 and the pad 194 on the extension clip 170 rotated. The second hub 104 remains relatively constant or steady so that the needle bevel 200 of the needle 106, which is attached to the second hub 104, faces upwardly to about the twelve o'clock position. As shown, the first hub 102 is rotated so that the tubing port 150 is at about the three o'clock position while the pad 194 is rotated to about the nine o'clock position. Again, the angular positions of the pad 194 and the tubing port 150, the latter if incorporated, can vary along the full arc gradient of a circle in increments that can be selected by incorporating a particular number of interference elements.

FIG. 6 shows a needle assembly 100 with an extension clip 170 having a grip extension 182 mounted over a second hub 104 having a needle 106 and a first hub 102 having a tube 105 but without a tubing port. Similar to other embodiments discussed elsewhere herein, the pad 194 on the grip extension 182 can be rotated along an arc circle relative to the second hub 104 to a position that is comfortable or desirable to a user. In the present embodiment, as in all other embodiments discussed elsewhere herein, a needle guard can optionally be incorporated for covering the needle tip 108 of the needle 106 following successful venipuncture. The extension clips 170 of FIGS. 3-6 can embody any number of structural features discussed herein for extension clips.

FIG. 7 is a perspective view of an exemplary extension clip or extension ring 170 having a grip extension 182 provided in accordance with aspects of the present disclosure. The grip extension 182 is similar to other grip extensions 182 discussed elsewhere herein, such as the grip extension 182 shown in FIG. 3. The clip ring 180 is shown with a slit 192 and an interior surface 188 comprising interior surface mating features 210 comprising a first interior detent guide 212, a second interior detent guide 214, and a plurality of interior interference elements 216. The interior surface mating features 210 are sized and shaped to mate with the exterior surface mating features 156 of a second hub 104, such as second hubs discussed elsewhere herein. Thus, as an example, if the exterior surface mating features 156 has a single detent guide and forty exterior interference elements, then the interior surface mating features 210 can also include a single corresponding detent guide and forty corresponding interference elements. Alternatively, the interior surface mating features 210 and the exterior surface mating features 156 have different or non-matching structural features. As previously described, this can reduce the rotational force, which can be more preferred in certain situations.

In an example, the first and second interior detent guides 212, 214 of FIG. 7 can each embody a raised detent or a recessed detent. In other examples, the two interior detent guides 212, 214 can be different, such as one being a recessed detent and the other one being a raised detent. Each raised detent can resemble two slanted edges that meet at an apex when looking at a cross-section, similar to a pyramid or a triangle. In still other examples, the raised detent can embody a different shape, such as a partial arc circle, a partial ellipse, a blade with a sharp or blunt edge, or a square cross-section. The recessed detent guide can be a negative of the raised detent guide. The detent guides 212, 214 of the clip ring 180 and the detent guides 160, 162 of the second hub 104 are sized and shape to engage one another, similar to a tongue-and-groove arrangement. Thus, if a detent guide on a clip ring 180 is a raised detent guide, then the detent guide on the second hub 104 is a recessed detent guide, and vice-versa. In some examples, only the first interior detent guide or the second interior detent guide is incorporated with the clip ring 180 but not both. In other examples, more than two interior detent guides are incorporated with the clip ring 180.

The interior interference elements 216 of the clip ring 180 can each embody a raised interference element, a recessed interference element, or combinations thereof. In an example, the interior interference elements 216 can each embody any number of geometrical shapes, polygonal shapes, irregular shapes, or custom shapes for use with exterior interference elements 156 on the second hub 104 having mating or corresponding shapes for engaging one another. As shown, the interference elements 216 have a raised diamond shape for engaging corresponding recessed diamond shaped interference elements on the second hub 104. In other examples, the interior interference elements 216 can have a square shape, an octagon shape, various gem shapes such as an asscher shape, a cushion shape, an emerald shape, a heart shape, a marquise shape, an oval shape, a pearl shape, a princess shape, a radiant shape, a round shape, a drop shape, a ball shape, a baguette shape, a mine shape, a rose shape, or a trillion shape. The interference elements 216 can alternatively have a gear shape, such as herringbone gear teeth or spur gear teeth. Thus, the listed examples are not to be viewed as limiting.

In some examples, the interior surface mating features and the exterior surface mating features do not precisely or accurately match, mate or correspond and the rotational features discussed herein still operable due to friction and interference between the various parts. For example, the interior interference elements 216 can have a raised diamond shape while the exterior interference elements 166 have a recessed oval shape. This non-precise matching of interference elements can still allow the ring clip 180 to rotate and be held at a particular angular position, possibly with some permissible slack or looseness. As another example, the detent guides 212, 214 on the clip ring 180 can have a triangle shape as projections while the detent guides 160, 162 on the second hub can have a square shape as recessed guides. Thus, the terms match, mate, and correspond are not limited to precision or exactness unless the context indicates otherwise.

The connection branch 193 attached to the clip ring 180 can have a variety of different geometrical shapes. In an example, the connection branch 193 extending from the body 184 of the clip ring 180 has a polygonal cross section, such as a square shape, a heptagon shape, or a decagon shape. The connection branch 193 can alternatively have a round, oval, elliptical, or irregular cross-section. The connection branch 193 is sufficiently thick and strong to withstand normal use without detaching, breaking, or otherwise separating from the clip ring 180. The connection branch 193 can have a uniform cross-sectional profile or can vary, such as in thickness, girth, and/or shape as it extends away from the clip ring 180. As shown, the connection branch 193 has a first connection section 220 and a second connection section 222, which has a changed direction from the first connection section. In other examples, the connection branch 193 has a single linear section extending at an angle from the exterior surface 196 of the clip ring 180 and the pad 194 extends from the single linear section. The connection branch 193 can have shapes that can be selected to provide sufficient clearance between the exterior surface 186 of the clip ring 180 and the inside edge 224 of the grip extension 182. The inside edge 224 of the pad can also be spaced from the exterior of the second hub.

The pad 194 extending from the connection branch 193 can have a regular, irregular, uniform, a non-uniform shape or combinations thereof. In an example, the pad 194 can be unitarily formed with the connection branch 193, which can be unitarily formed with the clip ring 180. The pad 194 can have distinct sections with distinct shapes, such as a base section 226 and a tip section 228 having the free end 196 and wherein the base section 226 and the tip section 228 have different geometrical shapes and sizes. In other examples, the pad 194 can have a single section with a single contour, such as a half of an oval, half of a square or rectangular shape, or half of a circle. In still other examples, the pad has more than three distinct sections. The distinct sections share an outer or outside edge 232 opposite the inside edge 224 with changing outer edge contours. In an example, at least the tip section 228 is sized and shaped to be gripped by a practitioner's fingers, such as by the thumb and the index finger, during venipuncture. In other examples, the pad 194 is selected with a shape that can be gripped by a user anywhere on the pad and not be limited to just the tip section 228 of the pad.

In some examples, the interior edge 224 can have a straight line. In other examples, the interior edge can have an undulating edge. The slit 192 on the clip ring 180 can be parallel to the interior edge 224. In other examples, they are not parallel or only parallel in-part. As shown, the slit 192 and the connection branch 193 can be located at diametrically opposed positions on the clip ring 180. In other examples, the two can be located less than 180 degrees from one another along the clip ring 180.

FIG. 8 is a cross-sectional side view of the extension clip or ring 170 of FIG. 7 taken along a plane defined by the slit 192 and the grip extension 182. As shown, the first and second interior detent guides 212 have two slanted edges that connect at an apex, similar to a triangle. The interior interference elements 216 are shown located between the first interior detent guide 212 and the second interior detent guide 214. In other examples, the two detent guides 212, 214 are located next to one another, such as near one of the open ends to the bore 190 and the interior interference elements 216 are located to one side of the pair of detent guides 212, 214. The two detent guides 212, 214, can form at the two openings of the bore 190 or both can be recessed inwards from the two end openings.

FIG. 9 is a cross-sectional side view of an extension clip 170 provided in accordance with further aspects of the present disclosure. The extension clip 170 of FIG. 9 is similar to the extension clip 170 of FIG. 7 with a few exceptions. In the present embodiment, the first and second interior detent guides 212, 214 have a single slanted edge and a vertical edge that connect forming a right angle at a base, similar to a right triangle. In other examples, the angle is not a right angle. The two vertical edges of the two interior detent guides 212, 214 can face the same direction or opposite directions. As shown, the two detent guides 212, 214 face the same direction. The two detent guides 212, 214 are recessed from the two end edges 240, 242 of the clip ring 180 but can be located at the end edges, as previously discussed. The two interior detent guides 212, 214 are configured to engage shaped exterior detent guides 160, 162 on a second hub or needle hub 104.

FIG. 10 is a cross-sectional side view of an extension clip or ring 170 provided in accordance with further aspects of the present disclosure. The extension clip 170 of FIG. 10 is similar to the extension clip 170 of FIG. 7 with a few exceptions. In the present embodiment, the first and second interior detent guides 212, 214 are curved or arcuate, resembling a dome. The two detent guides 212, 214 are recessed from the two end edges 240, 242 of the clip ring 180 but can be located at the end edges, as previously discussed. The two interior detent guides 212, 214 are configured to engage shaped exterior detent guides 160, 162 on a second hub or needle hub 104.

FIG. 11 is a perspective view of an extension clip 170 provided in accordance with further aspects of the present disclosure. The present extension clip 170 is similar to other extension clips discussed elsewhere herein and comprises interior surface mating features 210 for engaging corresponding exterior surface mating features 156 on a second hub 104. In the present embodiment, exterior gripping features 250 are provided, which can be raised channels, recessed channels or both. The exterior gripping features 250 resemble spur gears. In other examples, the exterior gripping features 250 can embody other shapes, such as an array of raised projections or bumps, recessed pockets, or combinations thereof. The exterior gripping features 250 can be molded features that are formed during molding of the extension clip 170 or separately formed and subsequently added to the exterior of the clip ring 180. For example, adhesive backed non-slip strips can be applied to the exterior of the clip ring 180 to facilitate gripping. Exterior surface mating features 250 can be incorporated with other extension clips discussed elsewhere herein.

FIG. 12 is a perspective view of a second hub 104 shown without a needle attached thereto. The second hub 104 is shown without a tubing port but one can optionally be included. The second hub 104 can be a needle hub and can be similar to other second hubs discussed elsewhere herein, such as the second hubs of FIGS. 1-6. The second hub 104 is shown with exterior surface mating features 156 for mating with interior surface mating features 210 on an extension clip 170. The surface mating features 156 can include a first exterior detent guide 160, a second exterior detent guide 162, and a plurality of exterior interference elements 166.

FIG. 13 is a cross-sectional side view of the second hub 104 of FIG. 12 taken along a lengthwise direction thereof. The present view clearly shows the recessed shapes of the first and second exterior detent guides 160, 162 and the exterior interference elements 166 of the exterior surface mating features 156 for engaging corresponding surface mating features on a clip ring 180 of an extension clip 170. The exterior surface mating features 156 can be formed when molding the second hub.

FIGS. 14-17 show different extension clip embodiments in accordance with aspects of the present disclosure. With reference to the extension clip 170 of FIG. 14, the interior surface mating features 210 include first and second interior detent guides 212, 214 and a plurality of interior interference elements 216. The first and second detent guides 212, 214 are shown with raised curved projections, similar to a half-dome. However, the first and second detent guides can embody other shapes, as previously described. The plurality of interior interference elements 216 are shown as raised triangular structures each with a base, two slanted sides, and an apex, similar to a triangular based pyramid or tetrahedron shape.

The extension clip or ring 170 of FIG. 15 is similar to that of FIG. 14 but wherein the plurality of interior interference elements 216 have a boomerang shape with two pairs of two slanted surfaces contacting one another to form two apexes.

The extension clip 170 of FIG. 16 is similar to that of FIG. 14 but wherein the plurality of interior interference elements 216 have a tetrahedron shape but with a curved base.

The extension clip 170 of FIG. 17 is similar to that of FIG. 14 but wherein the plurality of interior interference elements 216 have a raised strip with an enlarged projection in between the two ends of the raised strip. The enlarged projection can embody any number of different shapes including a diamond shape, a dome shape, or one of the several gem cut shapes.

FIG. 18 is a perspective view of an extension clip 170 provided in accordance with aspects of the present disclosure. The extension clip 170 can be similar to other extension clips described elsewhere herein. The extension clip 170 is shown with an enlarged grip extension 182 for discussion purposes. The connection branch 193 is shown with a first section 220 attached to the clip ring 180 and a second section 222 having the pad 194 extending therefrom. The connection branch 193 is generally uniform in cross-sectional shape along the length thereof. In an example, the connection branch 193 comprises a plurality of sides including a top side 260, two lateral sides 262, 264, and a bottom side 266. Four intersections are defined by the four sides 260-264. As shown, each intersection is curved, rounded or slanted to reduced high stress points. In other examples, the connection branch 193 does not have a uniform cross-section along the length thereof.

FIG. 19 is a partial perspective view of an extension clip 170 similar other extension clips described elsewhere herein. The connection branch 193 can be similar to the connection branch of FIG. 18. In the present embodiment, one or more raised ribs 270 can be provided with the connection branch 193, which can extend into part of the pad 194. As shown, two ribs 270 can be provided with one of the ribs 270 located on the top side 260 and another rib 270 on one of the lateral sides 262. In other examples, more than two ribs 270 can be provided. The ribs 270 can increase the strength of the grip extension 182 and make it less prone to breaking.

FIG. 20 is a partial perspective view of an extension clip 170 similar to other extension clips described elsewhere herein. The connection branch 193 can be similar to the connection branch of FIG. 18. In the present embodiment, one or more flange tabs 272 can be provided with the connection branch 193. Each flange tab 272 can act as a brace that connects to both the clip ring 180 and the connection branch 193. The flange tab 272 can have a triangular shape with two of the sides of the flange tab connected to the clip ring and the connection branch 193. As shown, one flange tab 272 is connected to the top side 260 of the connection branch 193 and the exterior of the clip ring 180 and another flange tab 272 is connected to the bottom side 266 of the connection branch 193 and the exterior of the clip ring 180.

FIG. 21 is a partial perspective view of an extension clip 170 similar to other extension clips described elsewhere herein. In the present embodiment, the connection branch 193 has an enlarged first section 220 compared to the second branch section 222. The enlarged first section 220 of the present embodiment provides additional girth and rigidity and a larger connection point with the clip ring 180 compared to other first branch sections, such as those shown in FIGS. 18-20. Thus, the connection branch 193 is understood to taper from a first dimension to a second dimension at the second branch section 222, which is smaller in cross-sectional dimension than the first dimension. Optionally, one or more ribs 270, one or more flange tabs 272, or combinations thereof may be incorporated to further reinforce the connection branch.

FIG. 22 is a partial perspective view of an extension clip 170 similar to other extension clips described elsewhere herein. In the present embodiment, the connection branch 193 has an enlarged first section 220 compared to the second branch section 222 and is similar to the connection branch 193 of FIG. 21. In the present embodiment, an anchor 280 is provided to reinforce the connection branch 193 to the clip ring 180. The anchor 280 provides a similar reinforcing function as the flange tabs 272 of FIG. 20 but with greater support due to the width and larger surface areas of the anchor 280 compared to the flange tabs 272. As shown, the anchor 280 has a vertical side 282 attached to the clip ring 180 and a bottom side 284 attached to the first section 220 of the connection branch 193. The anchor 280 further has two recessed or accurate side surfaces 286 and a slope front side 288. Optionally, the two side surfaces 286 are generally planar.

FIG. 23 is a perspective view of an extension clip or ring 170 provided in accordance with aspects of the present disclosure. The extension clip 170 can be similar to other extension clips described elsewhere herein, such as the extension clip of FIGS. 18-22. In the present embodiment, the exterior surface 186 of the clip ring 180 is provided with rotational instructions in the form of arrows 300. The arrows 300 can be embossed or raised surfaces provided as instructions for showing the direction of rotation of the clip ring 180. In other examples, the arrows 300 can be recessed surfaces formed into the body 184 of the clip ring. In some examples, exterior gripping features 250, similar to those shown in FIG. 11, can be included with the embossed or recessed instructions 300.

FIG. 24 is a cross-sectional side view of an extension clip 170 provided in accordance with further aspects of the present disclosure. The present extension clip 170 is similar to other extension clips described elsewhere herein. In the present embodiment, the grip extension 182 can include gripping features 310 on the surfaces of the pad 194. In an example, three spaced apart bumps or projections 312 can be provided on the first surface 314 and on the opposing surface (not shown) of the pad. The bumps 312 can be partially spherical in shape. In other examples, the number of bumps or projections can vary. In still other examples, the shape of the bumps can vary. The bumps 312 can be unitarily formed with the pad 194 or can be added to the pad.

FIG. 25 is a cross-sectional side view of an extension clip 170 provided in accordance with further aspects of the present disclosure. The present extension clip 170 is similar to other extension clips described elsewhere herein, including the extension clip of FIG. 24. In the present embodiment, the grip extension 182 can include gripping features 310 on the surfaces of the pad 194. In an example, three spaced apart bumps or projections 312 can be provided on the first surface 314 and on the opposing surface (not shown) of the pad. The bumps 312 of the present embodiment can embody elongated oval shaped surface mating features. In other examples, the number of bumps or projections can vary. In still other examples, the shape of the bumps can vary. The bumps 312 can be unitarily formed with the pad 194 or can be added to the pad.

In still other examples, the interior and exterior surface mating features 156, 210 can be without interference elements. For example, the detent guides 160, 162, 212, 214 can incorporate bumps or teeth to control angular rotation and alignment of the ring clip 180 without separately incorporating interference elements. In still other examples, the interior and exterior surface mating features can be without any detent guides. For example, the interference elements 166, 216 can engage one another to control angular rotation without the detent guides.

Methods of making and of using the needle devices and extension clips shown and described elsewhere herein are within the scope of the present disclosure.

Although limited embodiments of needle devices, extension clips, and their components have been specifically described and illustrated herein, many modifications and variations will be apparent to those skilled in the art. Furthermore, it is understood and contemplated that features specifically discussed for one extension clip embodiment may be adopted for inclusion with another extension clip embodiment, provided the functions are compatible. For example, while surface mating features are not discussed for the grip pad of FIG. 7, they can be included provided the functions do not conflict. Accordingly, it is to be understood that the needle devices and their components constructed according to principles of the disclosed devices, systems, and methods may be embodied other than as specifically described herein. The disclosure is also defined in the following claims.

What is claimed is:

1. A needle assembly comprising:
    a first hub having a tubing extending therefrom, said tubing having a lumen and a distal opening and said first hub comprising a body comprising an exterior surface and an interior surface defining an interior cavity;
    a second hub having a needle directly and fixedly attached to the second hub and extending therefrom, said needle comprising a needle tip with a needle bevel and said second hub comprising a body comprising an exterior surface with exterior surface mating features and an interior surface defining an interior cavity, said needle extending through the lumen with the needle tip extending distally of the distal opening of the tubing;
    an extension clip comprising a clip ring and a grip extension, said clip ring comprising a body comprising an exterior surface and an interior surface with spaced apart interior surface mating features and the body being mounted around the exterior surface of the second hub, and said grip extension comprising a pad having a free end; and
    wherein the interior surface mating features of the clip ring mate with exterior surface mating features of the second hub and the pad is at a first angular position and wherein the clip ring is rotatable relative to the second hub to change an angular position of the pad to a second angular position.

2. The needle assembly of claim 1, further comprising a needle guard located in the interior cavity of the first hub.

3. The needle assembly of claim 1, further comprising a tubing port extending from a side of the first hub.

4. The needle assembly of claim 1, wherein the exterior surface mating features comprise a detent guide.

5. The needle assembly of claim 4, wherein the exterior surface mating features comprise a plurality of spaced apart interference elements.

6. The needle assembly of claim 5, wherein the plurality of spaced apart interference elements comprise a plurality of raised interference elements.

7. The needle assembly of claim 5, wherein the plurality of spaced apart interference elements comprise a plurality of recessed interference elements.

8. The needle assembly of claim 4, wherein the exterior surface mating features comprise a second detent guide.

9. The needle assembly of claim 8, further comprising a plurality of spaced apart interference elements located between the detent guide and the second detent guide.

10. The needle assembly of claim 5, wherein the plurality of spaced apart interference elements are spaced from one another by a gap that limits the pad to rotation in two-degree to forty five-degree increments.

11. The needle assembly of claim 1, wherein the interior surface mating features comprise a detent guide recessed from an edge opening of the clip ring.

12. A needle assembly comprising:
    a first hub having a tubing extending therefrom, said tubing having a lumen and a distal opening and said first hub comprising a body comprising an exterior surface and an interior surface defining an interior cavity;
    a second hub having a needle extending therefrom, said needle comprising a needle tip with a needle bevel and said second hub comprising a body comprising an exterior surface with exterior surface mating features and an interior surface defining an interior cavity, said needle extending through the lumen with the needle tip extending distally of the distal opening of the tubing;
    an extension clip comprising a clip ring and a grip extension, said clip ring comprising a body comprising an exterior surface and an interior surface with interior surface mating features mounted around the exterior surface of the second hub, and said grip extension comprising a pad having a free end;
    wherein the interior surface mating features of the clip ring mate with exterior surface mating features of the second hub and the pad is at a first angular position and wherein the clip ring is rotatable relative to the second hub to change an angular position of the pad to a second angular position;
    wherein the interior surface mating features comprise a detent guide recessed from an edge opening of the clip ring;
    wherein the interior surface mating features further comprise a second detent guide recessed from a second edge opening of the clip ring.

13. The needle assembly of claim 1, wherein the clip ring is rotatable relative to the second hub while the needle bevel remains at a twelve o'clock position.

14. The needle assembly of claim 1, wherein the pad is movable relative to the second hub and from a three o'clock position to a nine o'clock position.

15. The needle assembly of claim 1, wherein said grip extension further comprises a connection branch connected to an exterior of the clip ring.

16. The needle assembly of claim 15, wherein the connection branch comprises a first section extending from the clip ring and a second section connected to the pad.

17. The needle assembly of claim 16, where the first section and the second section of the connection branch have the same cross-section.

18. The needle assembly of claim 16, wherein the first section of the connection branch has a larger cross-sectional dimension than a cross-sectional dimension of the second section.

19. The needle assembly of claim 15, further comprising at least one rib extending from a surface of the connection branch.

20. The needle assembly of claim 15, further comprising a flange tab attached to the clip ring and the connection branch.

21. The needle assembly of claim 15, further comprising an anchor attached to the clip ring and the connection branch.

22. The needle assembly of claim 1, further comprising exterior gripping features on the exterior surface of the clip ring.

23. The needle assembly of claim 22, wherein the gripping features comprise raised projections or bumps.

24. The needle assembly of claim 1, further comprising rotation instructions on the exterior surface of the clip ring.

25. The needle assembly of claim 24, wherein the rotation instructions comprises an arrow.

26. A needle assembly comprising:
a first hub having a tubing extending therefrom, said tubing having a lumen and a distal opening and said first hub comprising a body comprising an exterior surface and an interior surface defining an interior cavity;
a second hub having a needle extending therefrom, said needle comprising a needle tip with a needle bevel and said second hub comprising a body comprising an exterior surface with exterior surface mating features and an interior surface defining an interior cavity, said needle extending through the lumen with the needle tip extending distally of the distal opening of the tubing;
an extension clip comprising a clip ring and a grip extension, said clip ring comprising a body comprising an exterior surface and an interior surface with interior surface mating features mounted around the exterior surface of the second hub, and said grip extension comprising a pad having a free end;
wherein the interior surface mating features of the clip ring mate with exterior surface mating features of the second hub and the pad is at a first angular position and wherein the clip ring is rotatable relative to the second hub to change an angular position of the pad to a second angular position; and
wherein the interior surface mating features comprise two spaced apart raised detent rings and a plurality of raised interior interference elements.

27. The needle assembly of claim 26, wherein the raised interior interference elements each comprises a square shape, an octagon shape, an asscher shape, a cushion shape, an emerald shape, a heart shape, a marquise shape, an oval shape, a pearl shape, a princess shape, a radiant shape, a round shape, a drop shape, a ball shape, a baguette shape, a mine shape, a rose shape, a trillion shape or a gear shape.

28. The needle assembly of claim 27, wherein the gear shape comprises herringbone gear teeth or spur gear teeth.

29. The needle assembly of claim 26, wherein the two spaced apart raised detent rings each comprises a semi-spherical cross section, a square cross-section, a triangle cross-section, or a right triangle cross-section.

30. The needle assembly of claim 1, wherein the pad comprises a first surface and an opposed second surface and wherein a plurality of gripping features are incorporated with the first surface, the second surface, or both.

31. The needle assembly of claim 30, wherein the gripping features comprises a plurality of raised bumps or elongated oval bumps.

32. The needle assembly of claim 12, further comprising a needle guard located in the interior cavity of the first hub.

33. The needle assembly of claim 12, further comprising a tubing port extending from a side of the first hub.

34. The needle assembly of claim 12, wherein the exterior surface mating features comprise a detent guide.

35. The needle assembly of claim 34, wherein the exterior surface mating features comprise a plurality of spaced apart interference elements.

36. The needle assembly of claim 33, further comprising a tubing attached to the tubing port.

37. The needle assembly of claim 32, wherein the needle guard comprises a proximal wall with an opening and two arms extending distally of the proximal wall.

38. The needle assembly of claim 34, wherein the exterior surface mating features comprise a second detent guide.

39. The needle assembly of claim 38, further comprising a plurality of spaced apart interference elements located between the detent guide and the second detent guide.

40. The needle assembly of claim 37, wherein the needle comprises a crimp for engaging the opening on the proximal wall.

41. The needle assembly of claim 12, wherein the clip ring is rotatable relative to the second hub while the needle bevel remains at a twelve o'clock position.

42. The needle assembly of claim 12, wherein the pad is movable relative to the second hub and from a three o'clock position to a nine o'clock position.

43. The needle assembly of claim 12, wherein said grip extension further comprises a connection branch connected to an exterior of the clip ring.

44. The needle assembly of claim 43, wherein the connection branch comprises a first section extending from the clip ring and a second section connected to the pad.

45. The needle assembly of claim 43, where the first section and the second section of the connection branch have the same cross-section.

46. The needle assembly of claim 43, wherein the first section of the connection branch has a larger cross-sectional dimension than a cross-sectional dimension of the second section.

47. The needle assembly of claim 43, further comprising at least one rib extending from a surface of the connection branch.

48. The needle assembly of claim 43, further comprising a flange tab attached to the clip ring and the connection branch.

49. The needle assembly of claim 43, further comprising an anchor attached to the clip ring and the connection branch.

50. The needle assembly of claim 12, wherein the interior surface mating features comprise two spaced apart raised detent rings and a plurality of raised interior interference elements.

51. The needle assembly of claim 12, wherein the pad comprises a first surface and an opposed second surface and wherein a plurality of gripping features are incorporated with the first surface, the second surface, or both.

52. The needle assembly of claim 26, further comprising a needle guard located in the interior cavity of the first hub.

53. The needle assembly of claim 26, further comprising a tubing port extending from a side of the first hub.

54. The needle assembly of claim 53, further comprising a tubing attached to the tubing port.

55. The needle assembly of claim 52, wherein the needle guard comprises a proximal wall with an opening and two arms extending distally of the proximal wall.

56. The needle assembly of claim 55, wherein the needle comprises a crimp for engaging the opening on the proximal wall.

57. The needle assembly of claim 26, wherein the clip ring is rotatable relative to the second hub while the needle bevel remains at a twelve o'clock position.

58. The needle assembly of claim 26, wherein the pad is movable relative to the second hub and from a three o'clock position to a nine o'clock position.

59. The needle assembly of claim 26, wherein said grip extension further comprises a connection branch connected to an exterior of the clip ring.

60. The needle assembly of claim 59, wherein the connection branch comprises a first section extending from the clip ring and a second section connected to the pad.

61. The needle assembly of claim 59, where the first section and the second section of the connection branch have the same cross-section.

62. The needle assembly of claim 59, wherein the first section of the connection branch has a larger cross-sectional dimension than a cross-sectional dimension of the second section.

63. The needle assembly of claim 59, further comprising a flange tab attached to the clip ring and the connection branch.

64. The needle assembly of claim 26, wherein the pad comprises a first surface and an opposed second surface and wherein a plurality of gripping features are incorporated with the first surface, the second surface, or both.

* * * * *